Figure 1:
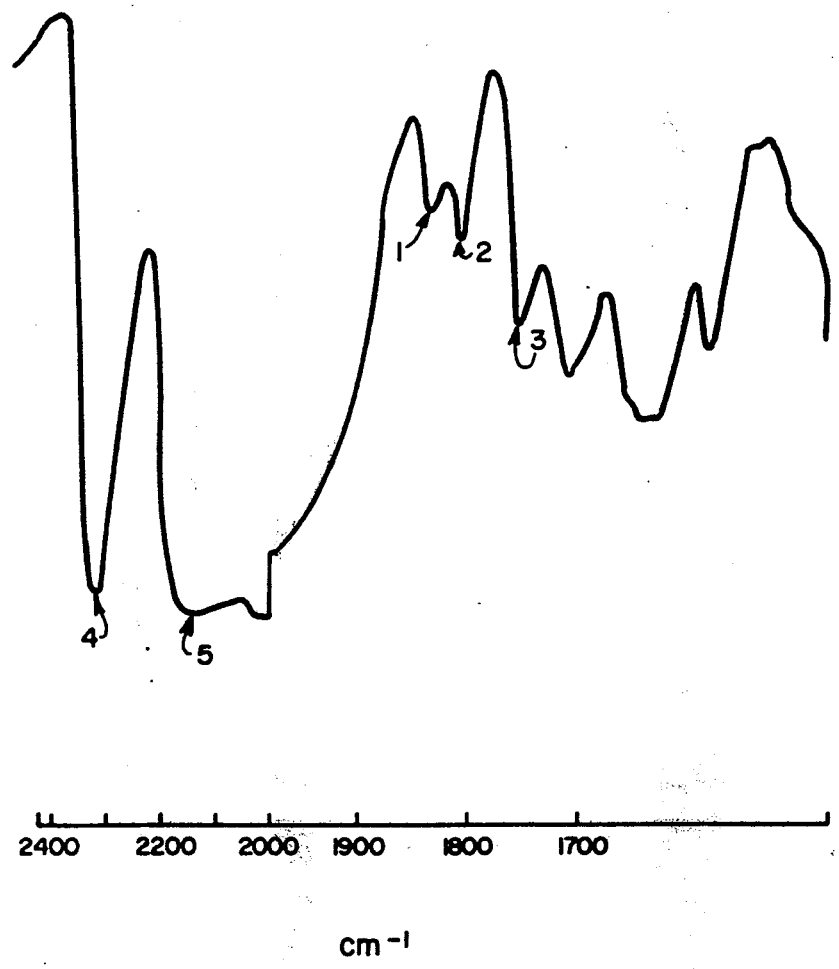

United States Patent [19]

Pruett et al.

[11] 3,957,857

[45] May 18, 1976

[54] CATALYTIC PROCESS FOR POLYHYDRIC ALCOHOLS AND DERIVATIVES

[75] Inventors: Roy L. Pruett; Wellington E. Walker, both of Charleston, W. Va.

[73] Assignee: Union Carbide Corporation, New York, N.Y.

[22] Filed: Apr. 18, 1974

[21] Appl. No.: 462,109

Related U.S. Application Data

[63] Continuation-in-part of Ser. No. 371,350, June 19, 1973, abandoned, which is a continuation-in-part of Ser. No. 219,130, Jan. 19, 1972, Pat. No. 3,833,634, which is a continuation-in-part of Ser. No. 210,538, Dec. 21, 1971, abandoned.

[52] U.S. Cl............................ 260/449; 252/431 R; 252/431 N; 252/443; 260/485 G; 260/488 J; 260/449.5; 260/449 L; 250/343; 23/230 A
[51] Int. Cl.$^2$.......................................... C07C 27/06
[58] Field of Search......... 260/449 R, 449 L, 449.5; 252/431 R, 431 W, 431 P, 443

[56] References Cited
UNITED STATES PATENTS

| | | | |
|---|---|---|---|
| 2,438,449 | 3/1948 | Mosesman | 260/449 R |
| 2,570,792 | 10/1951 | Gresham | 260/449 |
| 2,671,103 | 3/1954 | Kolbel et al. | 260/449 L |
| 2,692,274 | 10/1954 | Kolbel et al. | 260/449 L |
| 2,852,350 | 9/1958 | Kolbel et al. | 260/449 L |
| 3,081,357 | 3/1963 | Alderson et al. | 252/443 |
| 3,351,666 | 11/1967 | Mertzweiller et al. | 252/431 |
| 3,833,634 | 9/1974 | Pruett et al. | 260/449 R |

OTHER PUBLICATIONS

Martinengo et al., Gazz., 102 (1972) 344–354.

*Primary Examiner*—Howard T. Mars
*Attorney, Agent, or Firm*—George A. Skoler

[57] ABSTRACT

This invention relates to the manufacture of such valuable chemicals as polyhydric alcohols, their ether and ester derivatives, oligomers of such alcohols and monohydric alcohols and their ether and ester derivatives by reacting oxides of carbon and hydrogen in the presence of rhodium carbonyl clusters which possess an infrared spectrum which exhibit three intense wavelength bands between about plus and minus 10 $cm^{-1}$ of about 1868 $cm^{-1}$, about 1838 $cm^{-1}$, and about 1785 $cm^{-1}$.

17 Claims, 6 Drawing Figures

INFRARED SPECTRA OF RHODIUM COMPOSITION

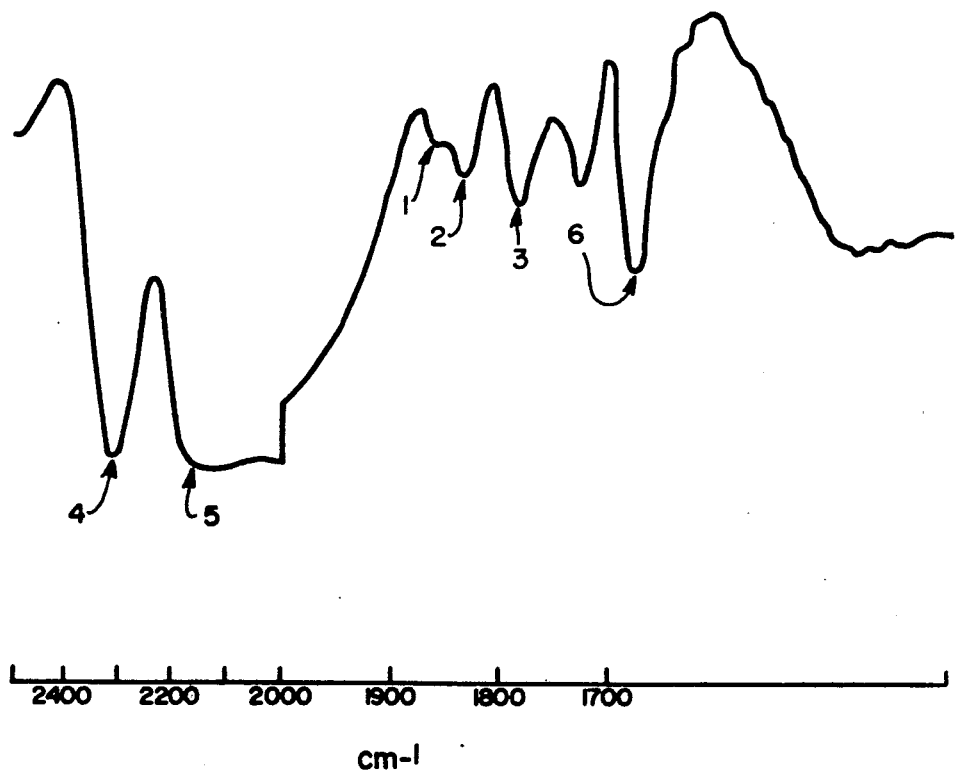
INFRARED SPECTRA OF RHODIUM COMPOSITION
F I G. 2

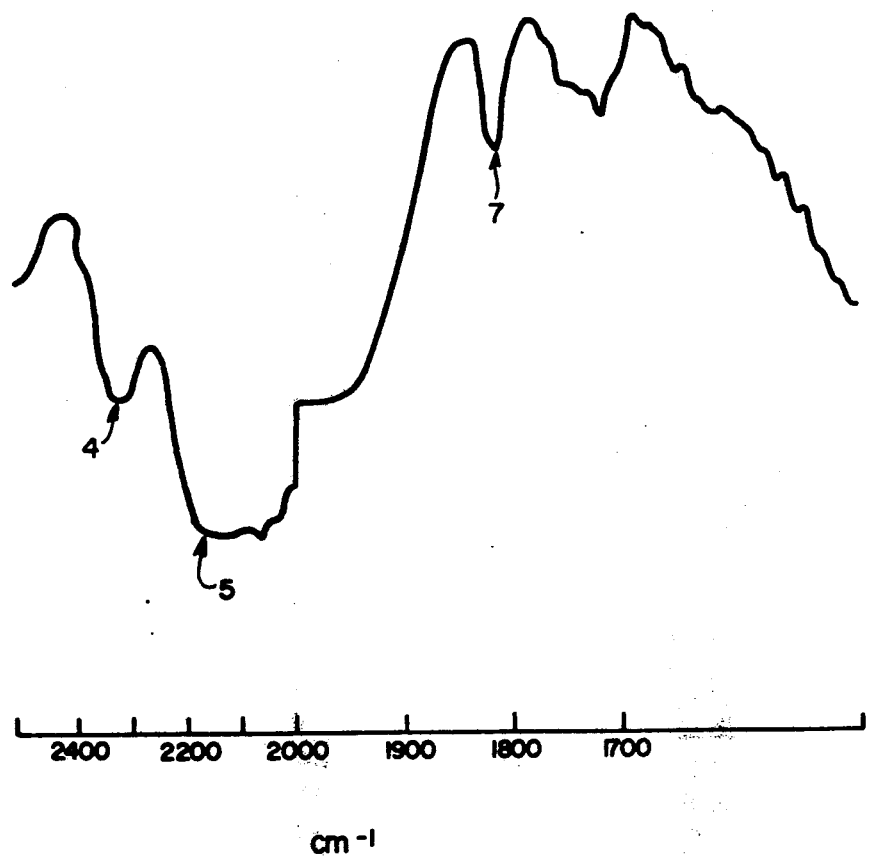
INFRARED SPECTRA OF RHODIUM COMPOSITION
F I G. 3

INFRARED SPECTRA OF RHODIUM COMPOSITION

INFRARED SPECTRA OF RHODIUM COMPOSITION

CATALYTIC PROCESS FOR POLYHYDRIC ALCOHOLS AND DERIVATIVES

This application is a continuation-in-part of copending application Ser. No. 371,350, filed June 19, 1973 and now abandoned, which is a continuation-in-part of Ser. No. 219,130 filed Jan. 19, 1972 now U.S. Pat. No. 3,833,634, which in turn is a continuation-in-part of application Ser. No. 210,538, filed Dec. 21, 1971 and now abandoned.

This invention is concerned with the manufacture of polyhydric alcohols, their ether and ester derivatives, and oligomers of such alcohols. This invention also produces monohydric alcohols such as methanol, and their ether and ester derivatives.

It is known that monofunctional compounds such as methanol can be obtained by reaction between carbon monoxide and hydrogen at elevated pressures, e.g., up to about 1000 atmospheres, and temperatures ranging from 250°C to 500°C, using mixtures of copper, chromium and zinc oxides as the catalyst therefor. It is disclosed in U.S. Pat. No. 2,451,333 that polyhydroxyl compounds are produced by reaction of formaldehyde, carbon monoxide, and hydrogen in the presence of hydrogenation catalysts. It has also been reported that formaldehyde can be produced by reaction between carbon monoxide and hydrogen at elevated pressures but repeated attempts to carry out this synthesis of formaldehyde have invariably failed to yield any substantial quantity of the desired product. It is generally recognized that the previously disclosed processes for the synthesis of formaldehyde from carbon monoxide and hydrogen at high pressures are either completely inoperative or else give rise to insignificantly small quantities of formaldehyde.

In British Pat. No. 655,237, published July 11, 1951, there is disclosed the reaction between carbon monoxide and hydrogen at elevated pressures and temperatures, e.g., above 1500 atmospheres at temperatures up to 400°C., using certain hydrogenation catalysts as exemplified by cobalt-containing compounds. U.S. Pat. Nos. 2,534,018; 2,570,792 and 2,636,046 are substantially similar in disclosure to the above said British patent. The only catalysts employed in the numbered examples of said U.S. Pat. No. 2,636,046 are those which contain cobalt.

It is also well-known that nickel is predominantly a catalyst for synthesis and for reforming methane according to the reaction

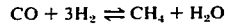

which proceeds from left to right at temperatures below about 500°C. and in the opposite direction at higher temperatures; see Kirk-Othmer, Encyclopedia of Chemical Technology, Second Edition, Volume 4, pages 452–453, John Wiley and Sons, New York (1964).

Polyhydric alcohols are presently being produced synthetically by the oxidation of petroleum derived materials. Owing to the limited availability of petroleum sources, the cost of these petroleum derived materials has been steadily increasing. Many have raised the dire prediction of a significant oil shortage in the future. The consequence of this has been the recognition of the need for a new low cost source of chemicals which can be converted into such polyhydric alcohols.

This invention is directed to the process of making polyhydric aliphatic alcohols, and to their ether, ester and oligomer derivatives. In particular, this invention is concerned with the manufacture of alkane polyols, most specifically, alkane diols and triols, containing 2 or 3 carbon atoms, their ethers, ester and oligomer derivatives. A by-product of this invention is the manufacture of the lesser valuable, but valuable nevertheless, monohydric alkanols such as methanol, ethanol and propanols, and their ether and ester derivatives. The products of the process of this invention contain carbon, hydrogen and oxygen.

This process involves the reaction of oxides of carbon and hydrogen in the presence of a rhodium carbonyl complex provided to the reaction as a rhodium carbonyl cluster which possesses an infrared spectrum which exhibits three intense wavelength bands between about plus and minus 10 cm$^{-1}$ of about 1868 cm$^{-1}$, about 1838 cm$^{-1}$, and about 1785 cm$^{-1}$ at a pressure of at least about 500 pounds per square inch absolute (psia). This means that the rhodium carbonyl cluster exhibits this infrared spectrum either during the reaction or at a temperature and/or pressure below that at which the reaction is effected. In both instances, the catalytic effect is achieved suggesting that the characterized rhodium clusters are always present.

P. Chini, in a review article entitled "The Closed Metal Carbonyl Clusters" published in Reviews (1968), Inorganica Chemica Acta, pages 31–50, states that a metal cluster compound is "a finite group of metal atoms which are held together entirely, mainly, or at least to a significant extent, by bonds directly between the metal atoms even though some non-metal atoms may be associated intimately with the cluster." The rhodium carbonyl cluster compounds of this invention contain rhodium bonded to rhodium or rhodium bonded to another metal, such as cobalt and/or iridium. The preferable rhodium carbonyl cluster compounds of this invention are those which contain rhodium-rhodium bonds. These compounds desirably contain carbon and oxygen in the form of carbonyl (—C—O), in which the carbonyl may be "terminal", "edge bridging" and/or "face bridging". They may also contain hydrogen and carbon in forms other than carbonyl. The following are structures of two rhodium carbonyl cluster usable in this invention:

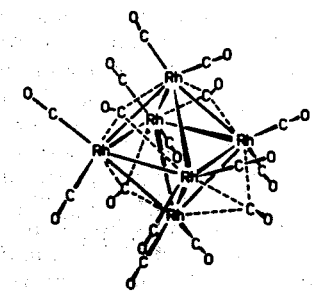

$Rh_6(CO)_{16}$

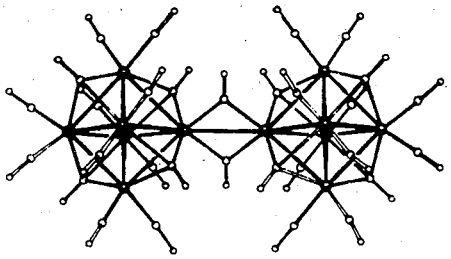

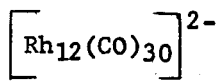

Rhodium carbonyl cluster ions which possess the infrared spectrum characterized previously, function in association with oxides of carbon and hydrogen, as herein defined, to produce the polyhydric alcohols etc. The exact mechanism by which the cluster compounds act to catalyze the reaction is not fully appreciated at this time. It is believed that the reaction is dependent upon the existance of the following equilibria:

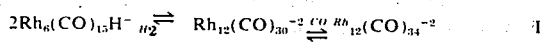

The clusters of this invention are ionic and they can be associated with any counter-ion provided that conditions are available by which a rhodium carbonyl cluster compound having aforedefined infrared spectrum characteristics is obtainable. The counter-ion may be rhodium per se, hydrogen, ammonia, any monovalent or polyvalent metal, and a broad range of organic compounds, such as those characterized as ligands.

The monovalent or polyvalent metal counter-ion may include lithium, sodium, potassium, rubidium, cesium, francium, beryllium, magnesium, calcium, strontium, barium, radium, scandium, yttrium, the rare earth metals (especially, e.g., cerium, praseodymium, and europium), titanium, zirconium, hafnium, manganese, rhenium, iron, ruthenium, osmium, cobalt, rhodium, iridium, nickel, palladium, platinum, copper, silver, gold, boron, aluminum, gallium, indium and thallium.

The organic counter-ions may result from "complexing" organic compounds with the rhodium carbonyl cluster ions or by ionically associating with the cluster.

The term "complex" means a coordination compound formed by the union of one or more electronically rich molecules or atoms capable of independent existence with one or more electronically poor molecules or atoms, each of which is also capable of independent existence. These organic rhodium cluster complexes are derived from the association of organic ligands with rhodium carbonyl solutions.

Organic ligands which are suitable in the practice of the invention contain at least one nitrogen atom (hereinafter called Lewis base nitrogen atom) and/or at least one oxygen atom (hereinafter called Lewis base oxygen atom), said atoms possessing a pair of electrons available for the formation of coordinate bonds with rhodium. Desirably, the organic ligand contains at least two Lewis base nitrogen atoms, or at least two Lewis base oxygen atoms, or at least one Lewis base nitrogen atom plus at least one Lewis base oxygen atom, said atoms possessing a pair of electrons available for the formation of coordinate bonds with rhodium, and said organic ligand forming with rhodium per se a chelate structure. In suitable embodiments the organic ligands contain from 2 and upwards to 4 Lewis base atoms, preferably from 2 to 3 such atoms, and most preferably 2 Lewis base atoms. These organic ligands are said to be multidentate or polydentate, that is to say, such ligands are bidentate, tridentate, or quadridentate, depending on whether 2, 3, or 4 Lewis base atoms are involved in the formations of chelate structures with rhodium.

Organic ligands which contain at least one Lewis base nitrogen atom will oftentimes hereinafter be referred to as "organic nitrogen ligands"; those ligands which contain at least one Lewis base oxygen atom will oftentimes be referred to as "organic oxygen ligands"; and those which contain at least one Lewis base nitrogen atom plus at least one Lewis base oxygen atom will oftentimes be referred to as "organic aza-oxa ligands".

Suitable organic nitrogen ligands most generally contain carbon, hydrogen, and nitrogen atoms. Suitable organic oxygen ligands most generally contain carbon, hydrogen, and oxygen atoms. Suitable organic aza-oxa ligands most generally contain carbon, hydrogen, oxygen, and nitrogen atoms. The carbon atoms can be acyclic and/or cyclic such as aliphatic, cycloaliphatic, aromatic (including fused and bridged) carbon atoms, and the like. Preferably, the organic ligands contain from 2 to 20 carbon atoms. The nitrogen atoms can be in the form of imino (—N=), amino (-N-),
       | nitrilo (N ≡ ), etc. Desirably, the Lewis base nitrogen atoms are in the form of imino nitrogen and/or amino nitrogen. The oxygen atoms can be in the form of groups such as hydroxyl (aliphatic or phenolic), $$\text{carboxyl } (-\overset{\overset{O}{\|}}{C}OH),$$

carbonyloxy $$(-\overset{\overset{O}{\|}}{C}O-),$$

oxy (—O—), $$\text{carbonyl } (-\overset{\overset{O}{\|}}{C}-),$$

etc.,
all of said groups containing Lewis base oxygen atoms. In this respect, it is the "hydroxyl" oxygen in the $$-\overset{\overset{O}{\|}}{C}OH \text{ group}$$

and the "oxy" oxygen in the

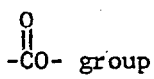
-CO- group that are the Lewis base atoms. The organic ligands may also contain other atoms and/or groups such as alkyl, cycloalkyl, aryl, chloro, thiaalkyl, trialkylsilyl, and the like.

Illustrative organic nitrogen ligands include for instance, N,N,N',N'-tetramethylethylenediamine, N,N,N',N'-tetraethylethylenediamine, N,N,N',N'-tetra-n-propylethylenediamine, N,N,N',N'-tetramethylmethylenediamine, N,N,N',N'-tetraethylmethylenediamine, N,N,N',N'-tetraisobutylmethylenediamine, piperazine, N-methylpiperazine, N-ethylpiperazine, 2-methyl-N-methylpiperazine, 2,2'-dipyridyl, methyl-substituted 2,2'-dipyridyl, ethyl-substituted 2,2'-dipyridyl, 1,4-diazabicyclo [2.2.2] octane, methyl-substituted 1,4-diazabicyclo [2.2.2] octane, purine, 2-aminopyridine, 2-(dimethylamino) pyridine, 1,10-phenanthroline, methyl-substituted 1,10-phenanthroline, 2-(dimethylamino)-6-methoxyquinoline, 7-chloro-1,10-phenanthroline, 4-triethylsilyl-2,2'-dipyridyl, 5-(thiapentyl)-1,10-phenanthroline, and the like.

Illustrative organic oxygen ligands include, by way of illustrations, glycolic acid, methoxyacetic acid, ethoxyacetic acid, digylcolic acid, thiodiglycolic acid, diether ether, tetrahydrofuran, dioxane, tetrahydropyran, pyrocatechol, citric acid, 2-methoxyethanol, 2-ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, oxetane, 1,2-diemthoxybenezene, 1,2-diethoxybenzene, methyl acetate, ethanol, 1,2-dimethoxyethane, 1,2-diethoxyethane, 1,2-di-n-propoxyethane, 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; the mono- and dialkyl ethers of propylene glycol, of diethylene glycol, of dipropylene glycol; and the like.

Illustrative organic aza-oxa ligands include, for example, ethanolamine, diethanolamine, isopropanolamine, di-n-propanolamine, N,N-dimethylglycine, N,N-diethylglycine, iminodiacetic acid, N-methyliminodiacetic acid, N-methyldiethanolamine, 2-hydroxypyridine, methyl-substituted 2-hydroxypyridine, picolinic acid, methyl-substituted picolinic acid, nitrilotriacetic acid, 2,5-dicarboxypiperazine, N-(2-hydroxyethyl) iminodiacetic acid, ethylenediaminetetraacetic acid, 2,6-dicarboxypyridine, 8-hydroxyquinoline, 2-carboxyquinoline, cyclohexane-1,2-diamine-N,N,N',N'-tetraacetic acid, the tetramethyl ester of ethylenediaminetetraacetic acid, and the like.

Other organic counter-ions are formed by ionic association with the rhodium carbonyl cluster ions. They are from organic compounds which possess Lewis base nitrogen atoms and typically are composed of carbon, hydrogen and nitrogen. Illustrative of such compounds are, e.g., piperidine, 2-methylpiperidine, 3-methylpiperidine, pyridine, 2-methylpyridine, 4-ethylpiperidine, triethylamine, benzyltrimethyl ammonium acetate and formate, tri-n-butylamine, dibutylamine, methylamine, dodecylamine, morpholine, aniline, benzylamine, octadecylamine, naphthylamine, cyclohexylamine, and the like.

FIGS. 1 – 5 depict the infrared spectra in the range of about 1500 $cm^{-1}$ to about 2400 $cm^{-1}$ of a number of rhodium containing compositions, with special emphasis of the range between 1700 $cm^{-1}$ and 2400 $cm^{-1}$.

With respect to FIG. 1, it depicts the infrared spectrum of a rhodium carbonyl 2-hydroxypyridine composition formed by adding 4 moles of 2-hydroxypyridine and 1 mole of rhodium in the form of $Rh(CO)_2$ acetylacetonate to a magnetically stirred autoclave to which was added carbon monoxide and hydrogen to a pressure of 10,500 psia at 210°C.

With respect to FIG. 2, it depicts the infrared spectrum of a rhodium carbonyl cluster composition formed by adding 4 moles of piperidine and 1 mole of rhodium in the form of $Rh(CO)_2$ acetylacetonate to a mechanically stirred autoclave to which was added carbon monoxide and hydrogen to a pressure of 10,500 psia at 210°C.

With respect to FIG. 3, it depicts the infrared spectrum of $Rh(CO)_2$ acetylacetonate added to a magnetically stirred autoclave to which was added carbon monoxide and hydrogen to a pressure of 10,500 psia at 210°C.

Figure 4:
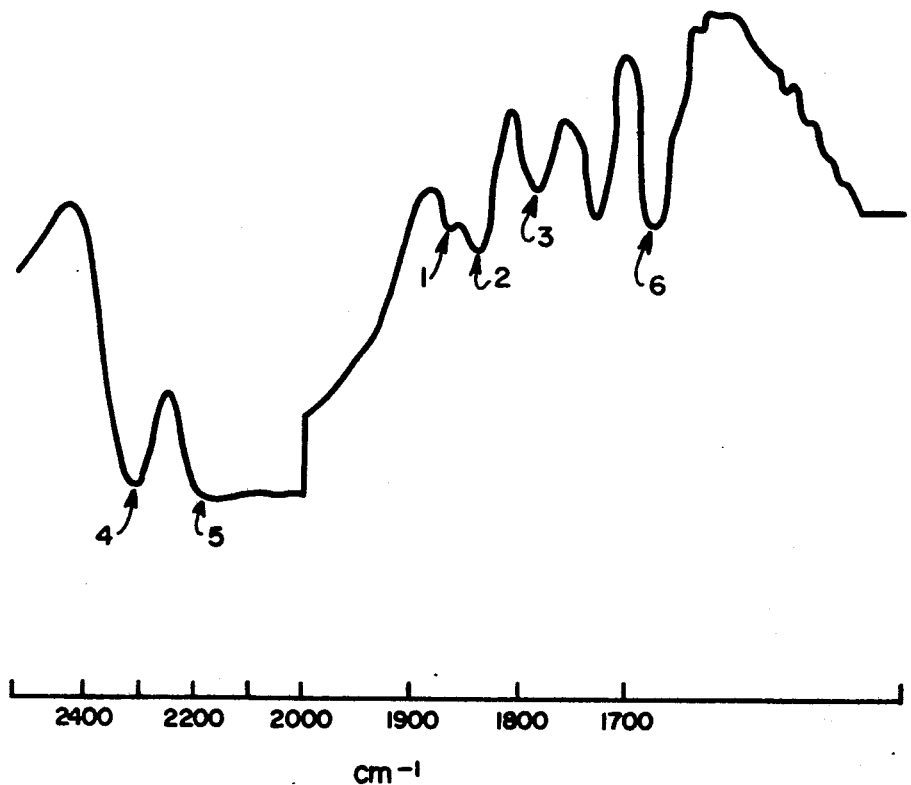

With respect to FIG. 4, it depicts the infrared spectrum of the same ingredients as treated with respect to FIG. 2 except that the pressure was 18,000 psia.

Figure 5:
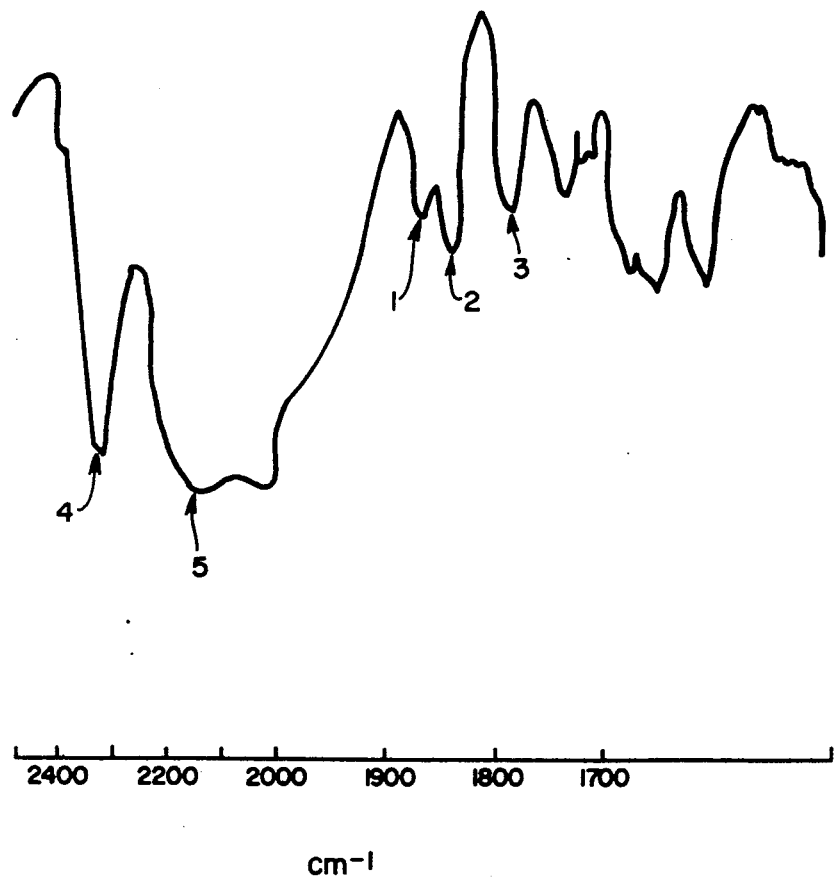

With respect to FIG. 5, it depicts the ingredients as treated with respect to FIG. 1 except that the pressure was 18,000 psia.

In each of the above runs depicted by FIGS. 1 – 5, the solvent (or diluent) was the dimethyl ether of tetraethylene glycol (tetraglyme) and the catalyst concentration was 1 percent based on the weight of rhodium present.

With respect to FIGS. 1, 2, 4 and 5, absorption bands 1, 2 and 3 are believed to represent the equilibria represented by equation (I) mentioned above. The intensity of these absorption bands in FIGS. 4 and 5 are believed to reflect a greater concentration of the $Rh_{12}(CO)_{34}{}^{-2}$ in the reaction mixture than is present in the spectrum of FIGS. 1 and 2. Absorption band 4 of FIGS. 1 – 5 are assignable to dissolved carbon dioxide and absorption band 5 of FIGS. 1 – 5 reflect the presence of dissolved carbon monoxide. Absorption band 6 of FIGS. 2 and 4 are assignable to the carbonyl stretching frequency of N-formylpiperidine.

Each of the examples defined by the spectra of FIGS. 1, 2, 4 and 5 is characteristic of a system capable of producing good quantities of polyhydric alcohol such as ethylene glycol. The spectrum of FIG. 3, however, shows the absorption band at 7 which is assignable to face bridging carbonyl frequency for the neutral complex of $Rh_6(CO)_{16}$. In this example, the conditions selected were not sufficient to create the equilibria characterized in equation (I). If the condition of the FIG. 3 example were raised to 25,000 psia, the equilibria equation (I) is obtainable.

Figure 6:
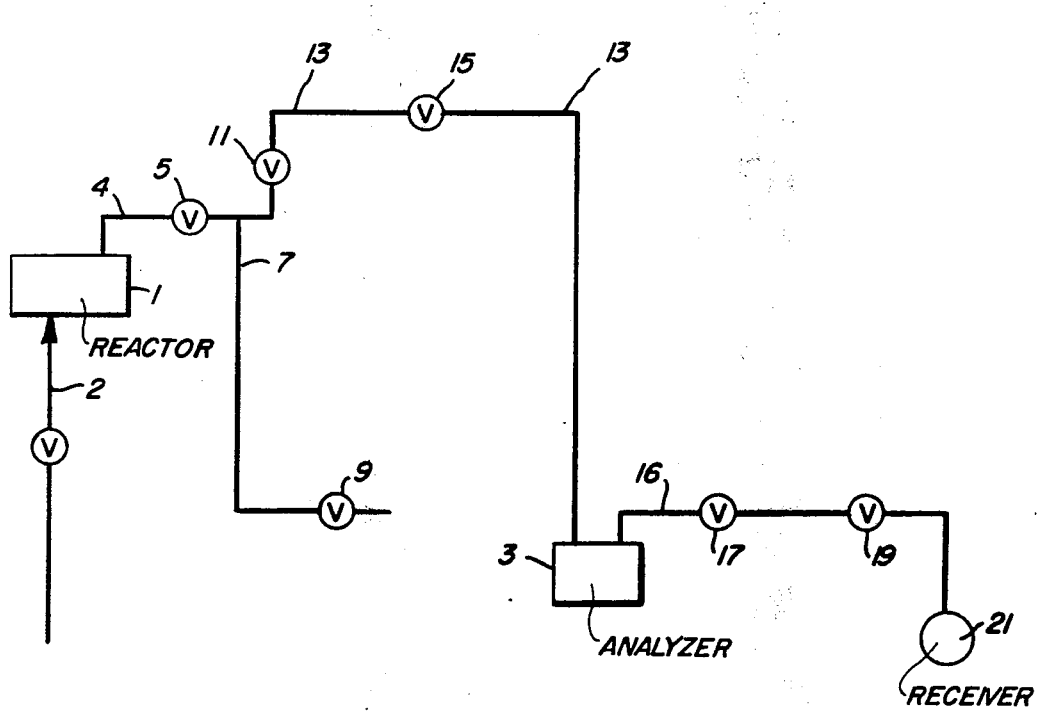

The equipment arrangement which provides the capability for determining the existance of rhodium carbonyl clusters having the aforedefined infrared spectrum characteristics, during the course of the manufacture of polyhydric alcohols and their derivatives, pursuant to this invention, is schematically depicted in FIG. 6 and described hereinafter.

With respect to FIG. 6, reactor 1 is connected to an infrared analyzer 3 and the product analyzed is collected in receiver 21. Reactor 1 is a stainless steel lined autoclave having an 150 cc. volume interior. The autoclave is equipped with a magnetic stirring device to minimize the possibility of gas leakage. The reactant feed is introduced through line 2 containing a shut-off valve. Reactant introduction is effected by hypodermic needle through a stainless steel sleeve and a gum rubber stopper. After the reaction is initiated, samples are withdrawn through heated tubing 4 after the reaction has reached a point when analysis is desired or the withdrawal is continuous from the time the desired reaction temperature is reached. One should not attempt to open, close and re-open tubing 4. Such intermittent withdrawals would result in depletion of carbon monoxide and catalyst metal plating out in the infrared cell. The withdrawal of materials from reactor 1 is effected through heated tubing 4 through heated shut-off valve 5, which has a 30,000 psi rating, through heated line 13, heated surge check valve 11 and heated shut-off valve 15, which has a 30,000 psi rating, to infrared analyzer 3. Should any problems occur in analyzer 3 which results in a sudden surge of product from the reactor, then surge check valve 11 serves to shut off line 13 and the excess product is passed through line 7 and emitted through vent valve 9, which also has a 30,000 psi rating.

The infrared analyzer used was a Perkin-Elmer Model 257 (Manufactured and sold by Perkin-Elmer Corporation, Norwalk, Connecticut 06856). The product is fed to a high pressure, high temperature infrared cell (not shown) from which the infrared scan is made by the analyzer. The cell should be constructed to withstand pressures of at least 30,000 psia and temperatures up to about 250°C. The cell window through which the scan is made should be properly sealed to withstand the high pressures employed. A particularly desirable infrared cell construction is described in U.S. Ser. No. 371,352, filed June 19, 1973, now abandoned, and Ser. No. 451,437, filed Mar. 15, 1974, which issued as U.S. Pat. No. 3,886,364, on May 27, 1975, and their disclosures of preferred cell construction is incorporated herein by reference. The product effluent from the cell is carried by line 16 containing 30,000 psi rated shut off valve 17 and 30,000 psi rated metering valve 19 to receiver 21.

The operation of the aforedefined high pressure infrared analyzer is as follows:

Reactor 1 is charged with the solvent to be used for the reaction (100–130cc). Reactor 1 is then pressurized with about 200 atmospheres of CO and $H_2$ and valves 5 and 15 are opened to pressurize the infrared cell in analyzer 3. Valve 17 is then opened and valve 19 is adjusted to give a small flow in order to make sure the excess surge check valve 11 has not closed. About 30 cc are purged through to flush the system. Valve 17 is then closed and the system is allowed to stand for 15 minutes to make sure an initial seal has been obtained on the cell (determined as no solvent leak in cell area by visual observation). After the initial seal has been made, the cell is sealed off by closing valves 5 and 15. The reactor 1 is then vented, dumped and recharged with the catalyst to be studied dissolved in 130 cc. of solvent. The reactor is then repressurized with 200 atmospheres of CO and $H_2$ mix to be studied and again connected to the cell by opening valves 5 and 15. The gas is then added to raise the pressure to a value ¾ of that desired at the reaction conditions of 210°–220°C.

If it is desired to obtain spectra only at reaction conditions, then heat is applied first to reactor 1 and it is brought to nearly reaction temperature before applying heat to lines 4, 13 and the infrared cell in 3. If it is desired to obtain spectra at temperatures lower than the final operating temperature, then heat is applied to reactor 1, the cell and the lines, and they are brought to the desired temperature at the same rate. The purge of the reactor and through the cell is started at room temperature. The analyzer's off and on, and scan, switches are remotely mounted in a control cubicle for reasons of safety. Thus, with a flow from the reactor through the cell a spectrum may be recorded anytime reactor, lines and cell are at the same temperature. The flow through the cell is regulated at about 1cc/minute and the volume of the system from reactor to final metering valve is approximately 10 cc, so that a spectrum may be recorded every ten minutes if so desired. Generally, reaction conditions are maintained for about 30 minutes while 3 to 4 spectra are recorded. CO and $H_2$ are added to the reactor to hold it at a constant pressure during this period of purging a continuous sample through the I R cell. The entire system is then slowly cooled and spectra may also be recorded during this cooling period. Flow through the system is stopped by closing all valves when the system has cooled to 120°–140°C.

The "oxide of carbon" as covered by the claims and as used herein is intended to mean carbon monoxide and mixtures of carbon dioxide and carbon monoxide, either introduced as such or in situ formed in the reaction.

In the practice of preferred embodiments of the invention a normally-liquid organic diluent is employed. Such diluents can be inert organic diluents, or they may be reactive diluents, and they can include the aforedescribed organic ligands, or mixtures thereof. Illustrative of the normally-liquid organic diluents which are generally suitable in the practice of desirable embodiments of the invention include, for example, saturated and aromatic hydrocarbons, e.g., hexane, octane, dodecane, naphtha, decalin, tetrahydronaphthalene, kerosene, mineral oil, cyclohexane, cycloheptane, alkylcycloalkane, benzene, toluene, xylene, naphthalene, alkylnaphthalene, etc.; ethers such as tetrahydrofuran, tetrahydropyran, diethyl ether, 1,2-dimethoxybenzene, 1,2-ethoxybenzene, the mono- and dialkyl ethers of alkylene glycols and polyalkylene glycols, such as ethylene glycol, of propylene glycol, of butylene glycol, of diethylene glycol, of dipropylene glycol, of triethylene glycol, of tetraethylene glycol of pentaethylene glycol, of dibutylene glycol, of oxyethyleneoxypropylene glycol, etc., preferably, those in which the alkylene group contains 2 carbon atoms in the divalent moeity, such as, ethylene and 1,2-propylene; carboxylic acids such as acetic acid, propionic acid, butyric acid, caproic acid, stearic acid, benzoic acid, cyclohexanecarboxylic acid, etc.; alkanols such as methanol, ethanol, propanol, isobutanol, 2-ethyl-hexanol, etc.; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; water; anhydrides such as phthalic anhydride, acetic anhydride, etc.; and others. Tetrahydrofuran, dioxane, and the mono and dialkylethers of triethylene and tetraethylene glycol are preferred diluents. It should be noted that the use of reactive diluents in the practice of desirable embodiments of the invention can give rise to a range of useful products. For instance, the mono- and diacetate esters of ethylene glycol can be obtained by using acetic acid as the diluent in the reaction medium. The use of alkanols, e.g., methanol and ethanol, can result in the monoalkyl ethers of ethylene glycol.

The quantity of catalyst employed is not narrowly critical and can vary over a wide range. In general, the novel process is desirably conducted in the presence of a catalytically effective quantity of the active rhodium species which gives a suitable and reasonable reaction rate. Reaction proceeds when employing as little as about $1 \times 10^{-6}$ weight percent, and even lesser amounts, of rhodium metal based on the total weight of reaction mixture. The upper concentration limit can be quite high, e.g., about 30 weight percent rhodium, and higher, and the realistic upper limit in practicing the invention appears to be dictated and controlled more by economics in view of the exceedingly high cost of rhodium metal and rhodium compounds. No particular advantages at the relatively high concentration of rhodium are manifest. Depending on various factors such as the counter-ion of choice, the partial pressures of oxides of carbon and hydrogen, the total operative pressure of the system, the operative temperature, the choice of the normally-liquid organic diluent, and other considerations, a catalyst concentration of from about $1 \times 10^{-5}$ to about $1 \times 10^{-1}$ weight percent rhodium (contained in the complex catalyst) based on the total weight of reaction mixture, is generally desirable in the practice of the invention.

The operative temperature which may be employed can vary over a wide range of elevated temperatures. In general, the novel process can be conducted at a temperature in the range of from about 100°C. and upwards to approximately 375°C, and higher. Operative temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, signs of some catalyst instability are noted. Notwithstanding this factor, reaction continues and polyhydric alcohols and/or their derivatives are produced. Additionally, one should take notice of the equilibrium reaction for forming ethylene glycol:

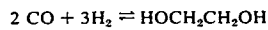

$$2\ CO + 3H_2 \rightleftharpoons HOCH_2CH_2OH$$

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher operative pressures, however, do not represent preferred embodiments of the invention in view of the high investment costs associated with erecting chemical plants which utilize high pressure utilities and the necessity of fabricating equipment capable of withstanding such enormous pressures. Suitable operative temperatures are between about 150°C. to about 300°C., and desirably from about 190°C. to about 275°C.

The novel process is suitably effected over a wide superatmospheric pressure range. At pressures below about 500 psia, the rate of desired product formation is quite slow, and consequently, relatively faster reaction rates and/or higher conversions to the desired product can be obtained by higher operative pressures, e.g., at a pressure of at least about 800 psia. Pressures as high as 50,000 psia, and higher, can be employed but with no apparent advantages attendant thereto which offset the unattractive plant investment outlay required for such high pressure equipment. In one embodiment of the invention, the upper pressure limitation is approximately 25,000 psia. Effecting the novel process below about 14,000 psia, especially below about 6,000 psia, results in cost advantages which are associated with low pressure equipment requirements. A suitable pressure range is from about 1000 psia to about 12,000 psia. The pressures referred to above represent the total pressure of hydrogen and oxides of carbon. In a preferred embodiment of the invention, rhodium complex catalyst is maintained in solution in the liquid reaction medium.

The novel process is effected for a period of time sufficient to produce the desired polyfunctional oxygen-containing products and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressure exerted by its components, the concentration and choice of diluent, and other factors. The synthesis of the desired product (s) by the reaction of hydrogen with an oxide of carbon is suitably conducted under operative conditions which give reasonable reaction rates and/or conversions.

The relative amounts of oxide of carbon and hydrogen which are initially present in the reaction mixture can be varied over a wide range. In general, the mol ratio of $CO:H_2$ is in the range of from about 20:1 to about 1:20, suitably from about 10:1 to about 1:10, and preferably from about 5:1 to about 1:5. It is to be understood, however, that molar ratios outside the aforestated broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "run-away" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with/without make-up carbon monoxide and hydrogen to the reactor. Recovery of the desired product can be achieved by methods well-known in the art such as by distillation, fractionation, extraction, and the like. A fraction comprising rhodium catalyst, generally contained in byproducts and/or normally-liquid organic diluent, can be recycled to the reaction zone, if desired. All or a portion of such fraction can be removed for recovery of the rhodium values or regeneration to the active rhodium species, if necessary. Fresh rhodium catalyst can be intermittently added to the recycle stream or directly to the reaction zone.

Either heterogeneous or homogeneous reaction mixtures may be employed in the practice of the invention. In preferred embodiments, rhodium catalysts as defined herein which are soluble in the reaction medium give outstanding results. However, the synthesis of polyhydric alcohols and/or derivatives thereof can be suitably effected by using such catalysts which are not homogeneously distributed throughout the reaction mixture. Solid catalysts which remain in place during the course of the reaction may be employed. Suspensions of liquid or solid catalysts in liquid and/or gaseous media may be employed. In suitable embodiments of the invention the rhodium catalyst can be used in combination with inert materials or contained or deposited on porous supports such as alumina, silica-alumina, silica gel, activated charcoal, titania, zirconia, zeolites as well as the zeolitic molecular sieves, pumice, kieselguhr, inert porous organic polymers, (e.g., reticulated cation exchange resin) and the like.

The active forms of the rhodium carbonyl clusters may be prepared by various techniques. They can be preformed and then introduced into the reaction zone. Alternatively, any of the host of rhodium-containing substances as well as the counter-ion forming substances can be introduced into the reaction zone and, under the operative conditions of the process (which of course includes hydrogen and carbon monoxide), the active rhodium carbonyl cluster can be generated in situ. Illustrative of rhodium-containing substances which can be conveniently introduced or placed in the synthesis zone include, for example, rhodium oxide ($Rh_2O_3$), tetrarhodium dodecacarbonyl, dirhodium octacarbonyl, hexarhodium hexadecacarbonyl ($Rh_6(CO)_{16}$), rhodium(II) formate, rhodium(II) acetate, rhodium(II) propionate, rhodium(II) butyrate, rhodium(II) valerate, rhodium(III) naphthenate, rhodium dicarbonyl acetylacetonate, rhodium tris(acetylacetonate), rhodium trihydroxide, indenylrhodium dicarbonyl, rhodium dicarbonyl (1-phenylbutane-1,3-dione), tris(hexane-2,4-dionato)rhodium(III), tris(heptane-2,4-dionato)rhodium(III), tris(1-phenylbutane-1,3-dionato)rhodium(III), tris(3-methylpentane-2,4-dionato)rhodium(III), tris(1-cyclohexylbutane-1,3-dionato)rhodium(III), finely divided rhodium metal, rhodium metal and rhodium-containing compounds deposited on porous supports or carriers such as those exemplified previously, and others.

The preparation of rhodium carbonyl cluster compounds is conveniently carried out in a diluent or mixture of diluents, e.g., benzene. Tetrarhodium dodecacarbonyl, though of limited solubility, can be added to the diluent in a finely divided form. Any of several of the rhodium-containing compounds illustrated previously can be employed in lieu of $Rh_4(CO)_{12}$. Organic ligands such as 2-hydroxypyridine or other counter-ion forming compounds can also be added thereto. The cluster forming reaction can be effected under a carbon monoxide pressure, with or without $H_2$, of about 1 to about 15 atmospheres, and higher, using a temperature of about 30°C. to about 100°C., for a period of time ranging from minutes to a few days, generally from about 30 minutes to about 24 hours. The resulting rhodium cluster compound contained in the organic diluent is catalytically active in this process. The compound contains rhodium in clustered combination with carbon monoxide and the counter-ion of choice. In preparing the aforesaid compounds, one can suitably employ from about 0.01 to about 20 moles of counter-ion forming compounds per mole of rhodium (contained in the rhodium compound used as a rhodium source). Ratios outside this stated range can be employed especially when it is desirable to use diluent quantities of the counter-ion forming compounds.

Solutions of the novel catalytically active rhodium compounds can be deposited on porous carriers or supports of the type illustrated previously. For example, the catalytically active solution can be poured on the carrier, or the carrier can be immersed in an excess of the liquid solution, with the excess being subsequently removed. The impregnated support or carrier is then maintained at a temperature sufficient to volatilize the diluent to permit drying of the impregnated carrier. A vacuum may also be applied.

In the following Examples, the term "parts" designates parts by weight (in grams). The term "efficiency" was determined as follows:

$$\text{Efficiency }(\%) = \frac{\text{Grams of polyhydric Alcohol Product Produced}}{\text{Grams of Liquid Oxygenated Products Produced}} \times 100$$

EXAMPLE 1

A 100 ml. capacity stainless-steel reactor capable of withstanding pressures up to 7000 atmospheres was charged with 0.52 part of rhodium dicarbonyl acetylacetonate dissolved in 45 parts of tetrahydrofuran. The reactor was sealed and charged with 1300 atmospheres of synthesis gas (mixture of hydrogen and carbon monoxide, molar ratio $H_2:CO = 1:1$). Heat was applied to the reactor and contents, when the temperature of the mixture inside the reactor reached 190°C, as measured by a suitably placed thermocouple, an additional 100 atmospheres of synthesis gas ($H_2:CO = 1:1$ mole ratio) was added. This addition was repeated at 200°, 210° and 220°C. At a reaction temperature of 230°C, additional synthesis gas was added until the pressure reached 3,400 atmospheres.

The temperature was maintained at 230° for a period of 4.5 hours. During this period of time additional synthesis gas was added whenever the total pressure dropped to 2,900 atmospheres; the amount of synthesis gas ($H_2:CO = 1:1$) added was sufficient to bring the total pressure to 3,400 atmospheres. Several such repressurizations were required.

After the 4.5-hour period, the vessel and contents were cooled to room temperature. The excess gases were vented, and the reaction produce mixture was removed. It measured 58 parts. Analysis by vapor phase chromatography proved the presence of 9.8 parts of ethylene glycol, 1.5 parts of propylene glycol, 1.5 parts of glycerine, along with methanol, water, and methyl formate. The efficiency to polyhydric compounds was 64%.

Example 2

A 10-ml. stainless-steel reactor, fitted with an internal thermocouple and attached to a rocker, was charged with 5.0 parts of water, 0.2 part of isopropanol and 0.13 part of rhodium dicarbonyl acetylacetonate. The reactor was charged with 2700 atmospheres of synthesis gas (mole ratio $H_2:CO = 1:1$) and heat was applied. At a temperature of 100°C, rocking was begun. The vessel and contents were maintained at 250°C. for 1.5 hours. During this period of time the pressure was maintained in the region of 2400–3000 atmospheres by periodic repressurizing with synthesis gas ($H_2:CO = 1:1$).

The vessel and contents were cooled and the excess gases were vented. The product contained ethylene glycol and propylene glycol.

Example 3

A 10-ml. stainless-steel reactor was charged with 4.5 parts of tetrahydrofuran and 0.13 parts of rhodium dicarbonyl acetylacetonate. The reaction was conducted as described in Example 2 except that the temperature was 225°C and the reaction time was 1 hour and 10 minutes.

The product, 7.0 parts, was shown by vapor phase chromatography to contain 1.3 parts of ethylene glycol.

Example 4

A 100-ml. stainless-steel reactor was charged with 40 parts of methanol, 4 parts of toluene and 0.65 part of rhodium dicarbonyl acetylacetonate. The reactor was sealed and the reaction was conducted as described in Example 1 except that the reaction temperature was 250°C. The product contained 4.3 parts of ethylene glycol.

Example 5

A 100-ml. stainless-steel reactor was charged with 40 parts of isopropanol and 0.65 part of rhodium dicarbonyl acetylacetonate. The reaction was conducted as described in Example 1 except that the reaction temperature was 250°C. The product, 53 parts, was shown to contain 3.6 parts of ethylene glycol.

Example 6

A 100-ml. stainless-steel reaction vessel, capable of withstanding pressures of 7000 atmospheres, was charged with 40 parts of ethanol anD 0.65 part of rhodium dicarbonyl acetylacetonate. The reaction was conducted as described in Example 1, eXcept that the reaction temperature was 250°C and the time of heating was 3.5 hours. The product was shown to contain ethylene glycol and minor amounts of ethylene glycol monoethyl ether.

Example 7

A 10-ml. stainless-steel reactor was charged with 5.5 parts of tetrahydrofuran and 1.0 part of 1% rhodium on alumina. The reactor was charged with 1500 atmospheres of synthesis gas (molar ratio $H_2:CO = 1:1$) and heat was applied. At 100°C, rocking was begun. The vessel and contents were maintained at a temperature of 230°C and a pressure range of 1300–1700 atmospheres for 4 hours. Periodic addition of synthesis gas ($H_2:CO = 1:1$) was required to maintain the required pressure.

The vessel and contents were cooled to ambient temperature. The excess gases were vented and the product was removed. Analysis showed the presence of 0.28 part of ethylene glycol.

Example 8

A 10-ml. vessel was charged with 5.5 parts of tetrahydrofuran and 0.12 part of stannous acetate. The reaction was conducted as described in Example 7, except that the heating period was 2 hours. The product contained no polyhydric alcohols.

Example 9

A 10-ml. reaction vessel was charged with 5.5 parts of tetrahydrofuran and 0.07 part of triruthenium dodecacarbonyl. The reaction was conducted as in Example 8. The product contained no polyhydric alcohols.

Example 10

A 10-ml. reaction vessel was charged with 5.5 parts of tetrahydrofuran and 0.075 part of palladium (II) acetylacetonate. The reaction was conducted as described in Example 8. The product contained no polyhydric alcohols.

Example 11

A 10-ml. reaction vessel was charged with 5.5 parts of tetrahydrofuran and 0.10 part of platinum (II) acetylacetonate. The reaction was conducted as described in Example 8. The product contained no polyhydric alcohols.

Example 12

A 10-ml. reaction vessel was charged with 5.5 parts of tetrahydrofuran and 0.025 part of cupric acetate. The reaction was conducted as described in Example 8. The product contained no polyhydric alcohols.

Example 13

A 10-ml. reactor was charged with 5.5 parts of tetrahydrofuran, 0.055 part of chromium hexacarbonyl and 0.049 part of dimanganese decacarbonyl. The reaction was conducted as described in Example 8. Analysis of the product showed no detectable amounts of polyhydric alcohols.

Example 14

A 10-ml. reactor was charged with 5.5 parts of tetrahydrofuran and 0.027 part of tetrairidium dodecarbonyl. The reaction was conducted as described in Example 8. Analysis of the product showed that the iridium did not catalyze the formation of polyhydric alcohols.

Example 15

A 10-ml. stainless-steel reactor was charged with 6.0 parts of water and 0.04 part of zinc oxide. The reaction was conducted as described in Example 8. The product contained no polyhydric alcohols.

Example 16

A 10-ml. stainless-steel reactor was charged with 6.0 parts of acetic acid and 0.2 part of lead tetraacetate. The reaction was conducted as described in Example 8. No polyhydric alcohols were detected in the product mixture.

Example 17

A 10-ml. stainless-steel reaction vessel was charrged with 6.0 parts of acetic acid and 0.043 part of dicobalt octacarbonyl. The reaction was conducted as described in Example 8. The product contained no ethylene glycol but traces of the mono-and diacetate of ethylene glycol were detected.

Example 18

A 10-ml. reaction vessel was charged with 4.5 parts of N-methyl-2-pyrrolidinone and 0.13 part of rhodium dicarbonyl acetylacetonate. The reaction was conducted as described in Example 2. The product contained substantial quantities of ethylene glycol.

Example 19

A 10-ml. stainless-steel reactor, fitted with an internal thermocouple and attached to a rocker, was charged with 5.5 parts of tetrahydrofuran, 0.10 part of rhodium dicarbonyl acetonylacetonate and 0.22 part of pyrocatechol. The reactor was sealed, charged with 400 atmospheres of synthesis gas (mole ratio $H_2$:CO = 1:1) and heat was applied. At a temperature of 100°C, rocking was begun. The temperature was maintained at 180°C for 20 hours. The pressure was maintained at 700–750 atmospheres by periodic addition of synthesis gas.

The vessel and contents were cooled to room temperature and the excess gases were vented. The product was analyzed by vapor phase chromatography and proved to contain significant quantities of ethylene glycol.

Example 20

A 10-ml. stainless-steel reaction vessel was charged with 5.5 parts of tetrahydrofuran, 0.13 part of rhodium decarbonyl acetylacetonate and 0.11 parts of pyrocatechol. The reaction was conducted as described in Example 8. Analysis of the reaction product mixture showed that 0.50 part of ethylene glycol was produced.

Example 21

A 10-ml. stainless-steel reaction vessel was charged with 4.5 parts of dioxane, 0.8 part of toluene and 0.13 part of rhodium dicarbonyl acetylacetonate. The reaction was conducted as described in Example 2, except that the pressure was maintained at 2700–3300 atmospheres.

The product, 7.5 parts, was analyzed and found to contain 0.73 part of ethylene glycol.

Example 22

A stainless-steel reactor of 100-ml. capacity was charged with 54.6 parts of o-dimethoxybenzene (veratrole) and 0.65 part of rhodium dicarbonyl acetylacetonate. The reaction was conducted as described in Example 5. The product was removed (70 parts) and analyzed. 5.1 parts of ethylene glycol were present.

Example 23

A 10-ml. reaction vessel was charged with 5 parts of tetraethylene glycol dimethyl ether and 0.13 part of rhodium dicarbonyl acetylacetonate. The reaction was conducted as described in Example 2. The product, 7.5 parts, was analyzed by vapor phase chromatography and found to contain 1.25 parts of ethylene glycol.

Example 24 a 10-ml. reactor was charged with 4.5 parts of dioxane, 0.9 part of toluene and 1.0 part of 5% by weight rhodium on carbon. The reaction was conducted as described in Example 2. The reaction product contained substantial quantities of ethylene glycol and propylene glycol.

Example 25

A 100-ml. stainless-steel reactor capable of withstanding pressures up to 7000 atmospheres was charged with 45 parts of tetrahydrofuran, 0.65 part of rhodium dicarbonyl acetylacetonate and 0.78 part of 2,2′-bipyridyl. The reactor was sealed and charged with 1300 atmospheres of synthesis gas (mole ratio $H_2$:CO = 1:1). Heat was applied to the reactor and contents. When the temperature inside the reactor reached 190°C, as measured by a suitably placed thermo-couple, an additional 100 atmospheres of synthesis gas ($H_2$/CO = 1:1) was added. This addition was repeated at 200°C, 210°C, and 222°C. At a reaction temperature of 230°C, additional synthesis gas was added until the pressure reached 3,400 atmospheres.

The temperature was maintained at 230°C for a period of 4.5 hours. During this period of time, additional synthesis gas was added whenever the total pressure dropped to 2900 atmospheres. The amount of synthesis gas ($H_2$/CO = 1:1) added was sufficient to bring the total pressure to 3,400 atmospheres. Several such repressurizations were required.

After the 4.5-hour period, the reactor and contents were cooled to room temperature. The excess gases were vented, and the reaction product mixture was removed. It measured 64 parts. Analysis by vapor phase chromatography proved the presence of 7.5 parts of ethylene glycol, 1.8 parts of propylene glycol, 2.0 parts of glycerine along with water, methanol, ethanol and methyl formate. The efficiency of polyhydric alcohols was 60%. Anaylsis of the unreacted, excess gases by mass spectrographic procedures proved the absence of any significant quantity of methane as a by-product.

Example 26

A 100-ml. stainless-steel reactor was charged with 45 parts of tetrahydrofuran, 0.65 part of rhodium dicarbonyl acetylacetonate and 0.43 part of piperazine. The reaction was conducted as described in Example 25. The reaction product mixture, 60 parts, contained 8.6 parts of ethylene glycol, 1.7 parts of propylene glycol, and 2.0 parts of glycerine.

Example 27

A 10-ml. stainless-steel reactor, fitted with an internal thermocouple and attached to a rocker, was charged with 5.5 parts of tetrahydrofuran, 0.13 part of rhodium dicarbonyl acetylacetonate and 0.144 part of 8-aminoquinoline. The reactor was charged with 1100 atmospheres of synthesis gas (mole ratio $H_2:CO = 1:1$) and heat was applied. At a temperature of 100°C, rocking was begun. The vessel and contents were maintained at 230°C for 2 hours. During this time the pressure was maintained in the region of 1300–1700 atmospheres by periodic repressurizing with synthesis gas ($H_2:CO = 1:1$).

The vessel and contents were cooled to room temperature. The excess gases were vented and the reaction product mixture was removed (6.5 parts). Analysis showed the presence of ethylene glycol in substantial quantity and traces of propylene glycol.

Example 28

A reaction is conducted as in Example 27, except that the organic nitrogen ligand employed is 1,10-phenanthroline. Substantial quantities of ethlene glycol are produced.

Example 29

A 10-ml. reaction vessel was charged with 5.5 parts of tetrahydrofuran, 0.13 part of rhodium dicarbonyl acetylacetonate and 0.09 part of 2-aminopyridine. The reaction was conducted as described in Example 27. The product contained ethylene glycol in substantial quantities (35% efficiency, based on carbon).

Example 30

A 10-ml. reaction vessel was charged with 5.5 parts of N,N,N',N'-tetramethylmethylenediamine and 0.050 part of rhodium dicarbonyl acetylacetonate. The reaction was conducted as described in Example 27. The product contained 0.2 part of ethylene glycol.

Example 31

A 10-ml. reaction vessel was charged with 5.5 parts of tetrahydrofuran, 0.13 part of rhodium dicarbonyl acetylacetonate and 0.12 part of N,N,N',N'-tetramethylethylenediamine. The reaction was conducted as described in Example 3. The product was analyzed and found to contain 0.64 part of ethylene glycol.

Example 32

A 100-ml. stainless-steel reactor was charged with 36 parts of dioxane, 9 parts of toluene, 0.8 part of pyridine and 1.3 parts of rhodium dicarbonyl acetylacetonate. The reaction was conducted as described in Example 4. The product (67 parts) contained 4.4 parts of ethylene glycol and a significant quantity of proppylene glycol. The unreacted gases were analyzed by mass spectrographic means and proved to contain no significant quantity of methane.

Example 33

A 100-ml. stainless-steel reactor was charged with 0.13 part of rhodium dicarbonyl acetylacetonate, 0.10 part of 2-hydroxypyridine and 45 parts of tetrahydrofuran. The reaction was conducted as described in Example 4. The product was analyzed and found to contain 6.3 parts of ethylene glycol, 2.5 parts of propylene glycol and 5.0 parts of glycerine. The efficiency to polyhydric alcohols was 92%.

Example 34

A 100-ml. stainless-steel reactor was charged with 22.5 parts of tetrahydrofuran, 0.73 part of 8-hydroxyquinoline and 0.65 part of rhodium dicarbonyl acetylacetonate. The reaction was conducted as described in Example 4. The product contained 14.4 parts of ethylene glycol, 6.7 parts of propylene glycol and 4.3 parts of glycerine. The efficiency to polyhydric alcohols was 85%.

Example 35

A 100-ml. stainless-steel reactor was charged with 45 parts of tetrahydrofuran, 0.65 part of rhodium dicarbonyl acetylacetonate and 0.84 part of pyridine-2,6-dicarboxylic acid. The reaction was conducted as described in Example 4. The product contained 8.6 parts of ethylene glycol, 1.7 parts of propylene glycol and 2.8 parts of glycerine.

Example 36

A 10-ml. reaction vessel was charged with 5.5 parts of tetrahydrofuran, 0.19 part of 8-hydroxyquinoline and 0.13 part of rhodium dicarbonyl acetylacetonate. The reaction was conducted as described in Example 27. The product contained substantial quantities of ethylene glycol and small quantities of propylene glycol and glycerine.

Example 37

A 10-ml. reaction vessel was charged with 5.5 parts of tetrahydrofuran, 0.13 part of rhodium dicarbonyl acetylacetonate and 0.19 part of nitrilotriacetic acid. The reaction was conducted as in Example 27. The product contained substantial quantities of ethylene glycol and a trace of propylene glycol.

Example 38

A 10-ml. reaction vessel was charged with 5.5 parts of tetrahydrofuran, 0.13 part of rhodium dicarbonyl acetylacetonate and 0.29 part of ethylene-diamine-tetraacetic acid. The reaction was conducted as described in Example 27. Ethylene glycol was produced in 60% efficiency.

Example 39

A 10-ml. stainless-steel reaction vessel was charged with 5.5 parts of tetrahydrofuran, 0.11 part of rhodium dicarbonyl acetylacetonate and 0.18 part of 2-hydroxypyridine. The reactor was pressurized with 500 atmospheres of synthesis gas (mole ratio $H_2:CO = 1:1$) and heat was applied. At 100°C, rocking was begun. The vessel and contents were maintained at a temperature of 230°C and a pressure of 820–880 atmospheres for a period of 2 hours. Periodic addition of synthesis gas ($H_2:CO = 1:1$) was required to maintain the required pressure.

The vessel and contents were cooled to ambient temperature. The excess gases were vented and the product was removed. Analysis proved the presence of substantial quantities of ethylene glycol.

Example 40

A 10-ml. stainless-steel reaction vessel was charged with 6.0 parts of N,N'-dimethylethanolamine and 0.05 part of rhodium dicarbonyl acetylacetonate. The reaction was conducted in a manner similar to that described in Example 27. The product was analyzed and found to contain significant quantities of ethylene glycol.

Example 41

A 100-ml. stainless-steel reaction vessel was charged with 23.4 parts of tetrahydrofuran, 24.0 parts of water, 0.21 part of rhodium dicarbonyl acetylacetonate and 0.19 part of 2-hydroxypyridine. The reaction was conducted in a manner similar to that described in Example 1. The product (52 parts) was analyzed and found to contain significant quantities of ethylene glycol.

Example 42

A 10-ml. reaction vessel was charged with 6.0 parts of N-methylmorpholine, 0.05 part of rhodium dicarbonyl acetylacetonate and 0.10 part of 2-hydroxypyridine. The reaction was conducted in a manner similar to that described in Example 27. The product contained substantial quantities of ethylene glycol and a smaller amount of propylene glycol.

Example 43

A 10-ml. reaction vessel was charged with 6.0 parts of N-methylmorpholine and 0.05 part of rhodium dicarbonyl acetylacetonate. The reaction was conducted in a manner similar to that described in Example 27. The product contained substantial quantities of ethylene glycol and a smaller amount of propylene glycol.

Example 44

A 100-ml. reaction vessel was charged with 45.0 parts of tetrahydrofuran, 0.65 part of rhodium dicarbonyl acetylacetonate and 2.2 parts of pyrocatechol. The reaction was conducted in a manner similar to that described in Example 1. The liquid product mixture was analyzed and found to contain 11.9 parts of ethylene glycol. The unreacted gases were analyzed by mass spectrographic means and found to contain no significant quantity of methane.

Example 45

A 250-ml. stainless-steel vessel equipped with stirring was charged with 90 parts of tetrahydrofuran, 1.3 parts of rhodium dicarbonyl acetylacetonate and 1.9 parts of 2-hydroxypyridine. The vessel is sealed, flushed with synthesis gas and pressurized with synthesis gas to 300 atmospheres (molar ratio $H_2:CO = 1:1$). Heat was applied and stirring begun. The temperature was maintained at 180°C for 41.5 hours. The pressure was maintained between 390 and 450 atmospheres by periodic addition of synthesis gas ($H_2:CO = 1:1$) as required.

The vessel and contents were cooled to room temperature and the excess gases were vented. The product, 96 parts, was removed and analyzed by vapor phase chromatography. Significant quantities of ethylene glycol were found to be present.

Example 46

A 100-ml. stainless-steel reaction vessel was charged with 36 parts of tetrahydrofuran, 10 parts of morpholine and 0.65 part of rhodium dicarbonyl acetyl acetonate. The reaction was conducted in a manner similar to that described in Example 1. The product, 62 parts, contained substantial quantities of ethylene glycol and propylene glycol.

Example 47

A 10-ml. reaction vessel was charged with 5.5 parts of tetrahydrofuran, 0.13 part of rhodium dicarbonyl acetylacetonate and 0.19 part of nitrilotriacetic acid. The reaction was conducted in a manner similar to that described in Example 27. The product contained substantial quantities of ethylene glycol.

Example 48

A 100-ml. stainless-steel reaction vessel was charged with 45 parts of tetrahydrofuran, 0.65 part of rhodium dicarbonylacetylacetonate and 0.65 part of pyridine-2-carboxylic acid. The reaction was conducted in a manner similar to that described in Example 1. The product amounted to 57 parts, of which 10.9 parts were ethylene glycol. Analysis of the unreacted gases proved the absence of any significant quantity of methane.

Example 49

A 100-ml. stainless-steel vessel was charged with 48 parts of methanol, 0.52 part of rhodium dicarbonyl acetylacetonate and 0.73 part of 8-hydroxyquinoline. The reaction was conducted in a manner similar to that described in Example 1. The product, 66 parts, contained 6.9 parts of ethylene glycol. The unreacted gas contained no significant quantity of methane.

Example 50

A 100-ml. stainless-steel vessel was charged with 36 parts of dioxane, 9 parts of toluene, 1.3 parts of rhodium dicarbonyl acetylacetonate and 1.1 parts of triethylenediamine. The reaction was conducted as described in Example 1. The produce mixture contained substantial quantities of ethylene glycol.

Example 51

A 10-ml. reaction vessel was charged with 5.5 parts of toluene and 0.2 part of rhodium dicarbonyl acetylacetonate. The reaction was conducted in a manner similar to that described in Example 27. The product contained ethylene glycol.

Example 52

A 10-ml. reaction vessel was charged with 5.5 parts of ethyl acetate and 0.2 parts of rhodium dicarbonyl acetylacetonate. The reaction was conducted in a manner similar to Example 27. The product was analyzed and found to contain 0.64 part of ethylene glycol.

Example 53

A 10-ml. reaction vessel was charged with a 6 parts of acetic acid and 0.2 part of rhodium dicarbonyl acetylacetonate. The reaction was conducted as described in Example 27. The product mixture contained significant quantities of ethylene glycol.

Example 54

A 150cc stainless steel reactor equipped with a magnetically driven stirrer and capable of withstanding pressures up to 4000 atmospheres was charged with 3 m moles rhodium dicarbonyl acetylacetonate, and 12.0 m moles 2-hydroxypyridine dissolved in 75 grams dimethyl ether of tetraethylene glycol (tetraglyme). The reactor was sealed and charged with 1000 atmospheres of synthesis gas (mixture of hydrogen and carbon monoxide, mole ratio of $H_2:CO = 60/40$). Heat was applied and the contents of the reactor were brought to a temperature of 220°C. as measured by an internal thermocouple. At this temperature the reactor pressure was 1333 atmospheres. This temperature was maintained for a period of 4 hours during which the pressure was maintained in the range 1260–1400 atmospheres by charging additional synthesis gas to replace that consumed during the reaction. Total pressure drop during the reaction was 1180 atmospheres, after which the reactor and contents were cooled to room temperature. The excess gases were vented and the reaction product weighing 101.6 grams was discharged. The liquid product was analyzed by gas-liquid chromatography (GLC) and found to contain 9.0 grams methanol, 1.5 grams methyl formate, 0.3 grams ethanol, 20.4 grams ethylene glycol, 1.3 grams ethylene glycol monoformate and 2.0 grams glycerine.

Example 55

Example 54 was repeated except that the solvent was monomethylether of triethylene glycol (methoxytriglycol) and the reaction time was 3 hours. Total gas uptake was 900 atmospheres. The recovered product weighed 106.8 grams. Analysis by GLC showed 7.7 grams methanol, 15.7 g. ethylene glycol and 2.9 grams glycerine in addition to methyl formate and ethanol.

Example 56

Example 54 was repeated except that the solvent was Methyl Carbitol and the reaction time was 3 hours. Total gas uptake was 827 atmospheres and the weight of discharged product was 94.7 grams. Analysis of the recovered product showed 4.4 grams methanol, 16.2 grams ethylene glycol and 3.2 grams glycerine in addition to methyl formate and ethanol.

Example 57

Example 54 was repeated except that the solvent was tetrahydrofuran, the temperature was 230°C and the reaction time was 3 hours. Total gas uptake was 1207 atmospheres and the recovered product mixture weighed 106.3 grams. Analysis of the product by GLC gave 6.6 grams methanol, 1.5 grams methyl formate, 0.9 g ethanol, 21.3 grams ethylene glycol and 3.1 grams glycerine.

Example 58

Example 54 was repeated except that piperidine was used in place of 2-hydroxypyridine. Total gas uptake was 1507 atmospheres and the recovered liquid product weighed 114.9 grams. Analysis of this product gave 17.4 grams methanol, 3.0 grams methyl formate, 1.0 gram ethanol, 13.9 grams ethylene glycol and 0.7 gram glycerine.

Example 59

The reactor of Example 54 was charged with 3.0 m mole rhodium dicarbonyl acetyacetonate and 12.0 m moles 2-hydroxypyridine dissolved in 75 g. tetraglyme. The reactor was sealed and charged with 1000 atmospheres of synthesis gas, $H_2/CO$ mole ratio of 35/65. The temperature of the reactor contents was brought to 230°C, where the pressure was 1333 atmospheres. The pressure was maintained at between 1260–1400 atmospheres for a period of 2 hours and consuming 500 atmospheres of gas. The reactor was cooled, vented of excess gases and discharged yielding 91.7 grams of liquid product. Analysis of this product showed 1.3 grams methanol, 0.3 gram methyl formate, 0.1 gram ethanol, 9.4 grams ethylene glycol and 2.6 grams glycerine.

Example 60

The charge to the stainless steel reactor was the same as in Example 59. The reactor was sealed and charged with 500 atmospheres of synthesis gas with a $H_2:CO$ molar ratio of 35/65. The reactor contents were brought to a temperature of 220°C where the pressure was 667 atmospheres. This temperature was maintained for a period of 2 hours during which the pressure was maintained at 630–700 atmospheres by periodic additions of synthesis gas. The total consumption during this period was 93 atmospheres of gas. The reactor was then cooled, vented and discharged yielding 76.0 grams of liquid product. Analysis of this product gave 0.8 gram methanol, 0.1 gram methyl formate and 2.4 grams ethylene glycol.

Example 61

Example 60 was repeated except that in place of 2-hydroxypyridine, 6 m moles of piperidine was used. The total pressure drop was 100 atmospheres and the discharged liquid product weighed 80.5 grams. Analysis of the product showed 3.0 grams methanol, 0.4 gram methyl formate and 0.4 gram ethylene glycol.

Example 62

Example 59 was repeated except that 3-hydroxypyridine was used in place of 2-hydroxypyridine. Total gas uptake was 413 atmospheres and the weight of recovered liquid product was 86.0 grams. Analysis of the product gave 2.8 grams methanol, 0.8 gram methyl formate and 6.1 grams ethylene glycol.

Example 63

Example 60 was repeated except that in place of 2-hydroxypyridine, 3-hydroxypyridine was used. Total gas uptake was 60 atmospheres and the weight of discharged product was 79.0 grams. Analysis of this product gave 1.9 grams methanol, 0.2 gram methyl formate and 0.8 gram ethylene glycol.

Example 64

Example 59 was repeated using 4-hydroxypyridine instead of 2-hydroxypyridine. Total gas uptake was 447 atmospheres and the weight of discharged product was 87.6 grams. Analysis of the product showed 2.8 grams methanol, 0.7 gram methyl formate, 0.2 gram ethanol, 8.5 grams ethylene glycol and 0.9 gram glycerine.

Example 65

Example 60 was repeated using 4-hydroxypyridine instead of 2-hydroxypyridine. Total gas uptake was 67 atmospheres and the weight of recovered product was 76.0 grams. The GLC analysis of the product showed 1.7 grams methanol, 0.2 grams methyl formate and 1.2 grams ethylene glycol.

Example 66

Example 60 was repeated using 2-pyridylcarbinol instead of 2-hydroxypyridine. Total gas uptake was 73 atmospheres and the weight of recovered liquid product was 81.6 grams. Analysis of the product showed 2.4 grams methanol, 0.2 gram methyl formate and 1.0 gram ethylene glycol.

Example 67

Example 59 was repeated except that 2,6-dihydroxypyridine was used instead of 2-hydroxypyridine. Total gas uptake was 180 atmospheres and the weight of liquid product was 79.8 grams. Analysis of the liquid showed 0.8 gram methanol, 0.1 gram methyl formate, 0.5 gram ethanol and 2.1 grams ethylene glycol.

Example 68

Example 60 was repeated using 2,6-dihyoxypyridine instead of 2-hydroxypyridine. Total gas uptake was 20 atmospheres and the liquid product weighed 75.6 grams. Analysis showed 0.1 gram methanol, 0.4 gram ethanol and 0.4 gram ethylene glycol.

Example 69

Example 59 was repeated except that 2-cyanopyridine was used instead of 2-hydroxypyridine. Total gas uptake was 473 atmospheres and the discharged liquid weighed 88.7 grams. Analysis of the liquid product gave 3.0 grams methanol, 0.7 gram methyl formate, 0.2 gram ethanol and 5.9 grams ethylene glycol.

Example 70

Example 60 was repeated except that 2-cyanopyridine was used in place of 2-hydroxypyridine. Total gas uptake was 80 atmospheres and the liquid product weighed 76.9 grams. analysis of this product gave 1.5 grams methanol, 0.1 gram methyl formate and 0.2 gram ethylene glycol.

Example 71

Example 59 was repeated except that 2-acetylpyridine was used instead of 2-hydroxypyridine. Total gas uptake was 447 atmospheres and the recovered liquid product weighed 82.5 grams. Analysis of this product gave 2.8 grams methanol, 0.8 gram methyl formate, 6.6 grams ethylene glycol and 0.5 gram glycerine.

Example 72

Example 60 was repeated except that 2-acetylpyridine was used instead of 2-hydroxypyridine. The pressure drop during the reaction was 80 atmospheres and the weight of recovered product was 76.6 grams. Analysis of this product showed 1.8 grams methanol, 0.2 gram methyl formate and 0.8 gram ethylene glycol.

Example 73

Example 59 was repeated except that 2-methoxypyridine was used instead of 2-hydroxypyridine. Total gas consumption was 500 atmospheres and the liquid product weighed 82.8 grams. Analysis of this product gave 1.8 grams methanol, 0.5 gram methyl formate, 0.1 gram ethanol, 7.9 grams ethylene glycol and 1.4 grams glycerine.

Example 74

Example 60 was repeated except that 2-methoxypyridine was used instead of 2-hydroxypyridine. Total gas uptake was 100 atmospheres and the recovered liquid product weighed 78.5 grams. Analysis of this product showed 1.5 grams methanol, 0.2 gram methyl formate and 1.5 grams ethylene glycol.

Example 75

Example 59 was repeated except that di-2-pyridylketone was used instead of 2-hydroxypyridine. Total gas uptake was 420 atmospheres and recovered product weight was 83.2 grams. Analysis of this product gave 3.2 grams methanol, 0.9 gram methyl formate, 0.1 gram ethanol and 5.7 grams ethylene glycol.

Example 76

Example 60 was repeated except that di-2-pyridylketone was used in place of 2-hydroxypyridine. Total gas uptake was 93 atmospheres and the recovered liquid weighed 81.8 grams. Analysis of this liquid gave 1.9 grams methyl, 0.2 gram methyl formate and 0.6 gram ethylene glycol.

Example 77

Example 59 was repeated except that 2,6-dimethoxypyridine was used instead of 2-hydroxypyridine. Total gas uptake was 247 atmospheres and the weight of discharged product was 80.1 grams. Analysis of this product gave 1.3 grams methanol, 0.3 gram methyl formate and 3.8 grams ethylene glycol.

Example 78

Example 60 was repeated except that 2,6-dimethoxypyridine was used instead of 2-hydroxypyridine. Total gas uptake was 13 atmospheres and the recovered liquid product weighed 74.7 grams. Analysis of the product showed 0.5 gram methanol and 0.2 gram ethylene glycol.

Example 79

Example 59 repeated except that 2-dimethylaminopyridine was used instead of 2-hydroxypyridine (2-HP). Total gas uptake was 427 atmospheres and the liquid product weighed 85.9 grams. Analysis of this product gave 2.8 grams methanol, 0.7 gram methyl formate, 0.3 gram ethanol and 6.4 grams ethylene glycol.

Example 80

Example 60 was repeated except that 2-dimethylaminopyridine was used instead of 2-HP. Total gas uptake was 87 atmospheres and the recovered liquid product weighed 80.1 grams. Analysis of this product showed 1.8 grams methanol, 0.2 gram methyl formate and 1.1 grams ethylene glycol.

Example 81

Example 59 was repeated except that O-anisidine was used instead of 2-hydroxypyridine. Total gas uptake was 267 atmospheres and the recovered liquid weighed 84.1 grams. Analysis of this liquid gave 1.6 grams methanol, 0.4 gram methyl formate and 3.4 grams ethylene glycol.

Example 82

Example 60 was repeated except that o-anisidine was used instead of 2-hydroxypyridine. Total gas uptake was 20 atmospheres and the weight of recovered product was 73.2 grams. Analysis of this product showed 0.3 gram methanol and 0.1 gram ethylene glycol.

Example 83

Example 59 was repeated except that 6.0 m moles piperidine was used instead of 2-hydroxypyridine. Total gas uptake was 360 atmospheres and the liquid product weighed 83.3 grams. Analysis of this product gave 3.4 grams methanol, 1.0 gram methyl formate and 6.0 grams ethylene glycol.

Example 84

Example 60 was repeated except that pyridine was used instead of 2-hydroxypyridine. Total gas uptake was 47 atmospheres and the recovered liquid product weighed 79.0 grams. Analysis of this product gave 1.3 grams methanol, 0.1 gram methyl formate and 0.1 gram ethylene glycol.

Example 85

Example 60 was repeated except that 6.0 m moles 1,8-naphthyridine was used instead of 2-hydroxypyridine. Total gas uptake was 100 atmospheres and the recovered liquid product weighed 77.2 grams. Analysis of this liquid product showed 2.4 grams methanol, 0.2 gram methyl formate and 1.2 grams ethylene glycol.

Example 86

A 150 cc stainless steel reactor equipped with a magnetically driven stirrer and capable of withstanding pressures up to 4000 atmospheres was charged with 2 m moles rhodium dicarbonyl acetylacetonate and 30 m moles magnesium acetate dissolved in 55 grams of dimethoxytetraethylene glycol (tetraglyme) and 20 grams of water. The reactor was sealed and charged with 930 atmospheres of synthesis gas (mixture of hydrogen and carbon monoxide, mole ratio $H_2:CO = 60/40$). Heat was applied and the contents of the reactor were brought to a temperature of 210°C. as measured by an internal thermocouple. At this temperature the reactor pressure was 1200 atmospheres. This temperature was maintained for a period of 4 hours during which the pressure was maintained in the range 1160 – 1240 atmospheres by charging additional synthesis gas to replace that consumed during the reaction. Total pressure drop during the reaction period was 547 atmospheres after which the reactor and contents were cooled to room temperature. The excess gases were vented and the reaction product mixture was discharged. The liquid product weighed 84.1 grams and analysis by gas-liquid chromatography (GLC) proved the presence of 6.5 grams methanol, 5.6 grams ethylene glycol, 0.6 gram propylene glycol along with small amounts of methyl formate, ethanol and glycerine.

Example 87

Example 86 was repeated except that the mole ratio of $H_2/CO$ was 40/60. Total pressure drop during the 4 hour reaction period was 487 atmospheres and the liquid product weighed 83.8 grams. Analysis showed the presence of 2.7 grams methanol, 4.6 grams ethylene glycol, 0.6 gram ethylene glycol monoformate and 1.3 grams propylene glycol.

Example 88

Example 86 was repeated except that instead of magnesium acetate, 10 m moles of magnesium lactate was used. Total gas uptake was 480 atmosphere and the liquid product weighed 89.0 grams. Analysis by GLC gave 4.2 grams methanol, 6.6 grams ethylene glycol, 1.3 grams propylene glycol and 0.4 gram glycerine.

Example 89

Example 86 was repeated except that instead of magnesium acetate, 10 m moles of aluminum lactate was used. Total gas uptake was 587 atmospheres and the liquid product weighed 78.5 grams. Analysis gave 2.1 grams methanol, 7.0 grams ethylene glycol, 1.6 grams propylene glycol and 0.2 g. glycerine.

Example 90

Example 86 was repeated except that instead of magnesium acetate, 10.0 m moles of calcium lactate was used. Total pressure drop was 560 atmospheres and the liquid product weighed 90.0 grams. The analysis was 5.9 grams methanol, 7.9 grams ethylene glycol, 0.9 g propylene glycol and 0.3 gram glycerine.

Example 91

Example 90 was repeated except that the temperature was maintained at 215°C. The gas uptake was 673 atmospheres and the liquid product weighed 89.3 grams. Analysis showed 4.9 grams methanol, 9.4 grams ethylene glycol, 1.2 grams propylene glycol and 0.1 gram glycerine.

Example 92

Example 90 was repeated except that the temperature was maintained at 220°C. The gas uptake was 627 atmospheres and the liquid product weighed 93.8 grams. Analysis gave 4.3 grams methanol, 8.8 grams ethylene glycol, 1.7 grams propylene glycol and 0.1 grams glycerine.

Example 93

Example 90 was repeated except that the solvent used was 55 grams methoxytriglycol and 20 grams water. Total gas uptake was 540 atmospheres and the liquid product weighed 88.2 grams. Product analysis showed 7.8 grams methanol, 5.0 grams ethylene glycol and 0.7 gram propylene glycol.

Example 94

Example 90 was repeated except that the solvent was 55 grams Methyl Carbitol and 20.0 grams water. Total gas uptake was 580 atmospheres and the liquid product weighed 93.0 grams. Analysis gave 7.7 grams methanol, 6.4 grams ethylene glycol, 0.8 gram propylene glycol and 0.5 gram glycerine.

Example 95

The conditions of example 86 were used except that instead of magnesium acetate, aluminum citrate was used. The total gas uptake was 200 atmospheres and the recovered liquid product weighed 73.1 grams. Analysis by GLC showed 1.8 grams methanol, 2.2 grams ethylene glycol and 0.2 gram propylene glycol.

Example 96

Example 86 was repeated except that instead of magnesium acetate, magnesium glycolate was used. The total gas used was 453 atmospheres and the liquid product recovered weighed 76.9 grams. Analysis showed 2.3 grams methanol, 4.6 grams ethylene glycol, 1.0 gram propylene glycol and 0.5 gram glycerine.

Example 97

Example 89 was repeated except that the solvent was 75 grams tetraglyme free of water. The total gas uptake was 200 atmospheres and the liquid product weight was 74.0 grams. Analysis showed 2.2 grams methanol, 1.4 grams ethylene glycol and 0.1 gram propylene glycol.

Example 98

Example 86 was repeated except that instead of magnesium acetate, cerous acetate was used and the mole ratio of $H_2:CO$ was 40/60. Total gas uptake was 133 atmospheres and the weight of the discharged product was 66.7 grams. Analysis of the reaction mixture showed 1.2 grams methanol, 2.2 grams ethylene glycol and 0.7 gram propylene glycol.

Example 99

Example 86 was repeated except that instead of magnesium acetate, uranyl acetate was used and the mole ratio of $H_2$:CO was 40/60. The total pressure drop was 313 atmospheres and the discharged product mixture weighed 83.4 grams. Analysis showed 1.0 gram methanol, 1.2 grams ethylene glycol, 1.1 grams propylene glycol and 0.1 gram glycerine.

Example 100

Example 86 was repeated except that in place of rhodium dicarbonyl acetyl acetonate and magnesium acetate, $Mg[Rh_{12}(CO)_{30}]$ (2 m moles contained rhodium) was used. Total pressure drop was 253 atmospheres and the recovered product weighed 74.8 grams. Analysis showed the product to contain 1.1 grams methanol, 3.1 grams ethylene glycol and 0.9 gram propylene glycol.

Example 101

Example 100 was repeated except that the solvent was 75 grams tetraglyme free of water. Total gas uptake was 140 atmospheres and the discharged product weighed 72.6 grams. Analysis of the product showed 2.4 grams methanol and 0.3 gram ethylene glycol.

Example 102

Example 86 was repeated except that in place of rhodium dicarbonyl acetylacetonate and magnesium acetate, $Al_2[Rh_{12}(CO)_{30}]_3$ (2 m moles contained rhodium) was used. Total pressure drop was 293 atmospheres and the weight of recovered product was 84.2 grams. Analysis showed the product to contain 1.2 grams methanol, 3.8 grams ethylene glycol, 0.8 gram propylene glycol and 0.2 gram glycerine.

Example 103

Example 86 was repeated except that instead of magnesium acetate, 10.0 m mole barium acetate was used and the temperature was maintained at 215°C. Total gas uptake was 233 atmospheres and the product weight was 83.2 grams. Analysis showed 2.1 grams methanol, 2.7 grams ethylene glycol and 0.1 gram propylene glycol.

Example 104

Example 86 was repeated except that instead of magnesium acetate, 20.0 m moles strontium acetate was used and the temperature was maintained at 215°C. Total gas consumed was 87 atmospheres and the product weight was 64.9 grams. Analysis showed 1.4 grams methanol and 1.1 grams ethylene glycol.

Example 105

Example 86 was repeated except that instead of magnesium acetate, 20.0 m moles zinc acetate was used and the temperature was maintained at 215°C. The weight of discharged product was 73.5 grams and the total pressure drop was 100 atmospheres. The analysis showed 0.9 grams methanol and 0.8 gram ethylene glycol.

Example 106

Example 86 was repeated except that instead of magnesium acetate, sodium acetate (33.0 m moles) was used and the temperature was 215°C. Total gas uptake was 533 atmospheres and the weight of discharged product was 90.5 grams. Analysis gave 12.0 grams methanol, 0.4 gram methyl formate and 2.4 grams of ethylene glycol.

Example 107

Example 86 was repeated except that instead of magnesium acetate, sodium borate (10.0 m moles) was used and the temperature was 215°C. Total gas uptake was 293 atmospheres and the product weight was 77.9 grams. Analysis showed the product to contain 7.3 gram methanol, 0.6 gram methyl formate, 0.6 gram ethanol and 0.5 gram ethylene glycol.

Example 108

Example 86 was repeated in 75 grams tetraglyme (free of water) using instead of magnesium acetate, sodium phenoxide (12.0 m moles) at 215°C. Total gas uptake was 577 atmospheres and the recovered product weighed 88.2 grams. Analysis of the product showed 9.8 grams methanol, 2.3 grams methyl formate, 0.3 gram ethanol and 0.9 gram ethylene glycol.

Example 109

Example 86 was repeated in 75 grams of tetraglyme (free of water) using instead of magnesium acetate, sodium methoxide (12.0 m moles) at 215°C. Total gas uptake was 373 atmospheres and the recovered product weighed 82.7 grams. Analysis of the product gave 7.2 grams methanol, 2.1 grams methyl formate, 0.4 gram ethanol and 0.8 ethylene glycol.

Example 110

Example 86 was repeated except that instead of magnesium acetate, lithium acetate was used, and the temperature was maintained at 215°C. Total gas uptake was 473 atmospheres and the recovered product weight was 88.9 grams. Analysis of the product showed 11.8 grams methanol, 0.8 gram methyl formate, 0.6 gram ethanol and 2.1 grams ethylene glycol.

Example 111

Example 86 was repeated except that instead of magnesium acetate, cesium acetate was used and the reaction temperature was 215°C. Total gas uptake was 493 atmospheres and the recovered product weighed 83.6 grams. Analysis showed 10.9 grams methanol, 0.6 gram methyl formate, 0.1 gram ethanol and 0.7 gram ethylene glycol.

Example 112

Example 86 was repeated except that instead of magnesium acetate, cesium formate was used and the reaction temperature was 215°C. Total gas uptake was 607 atmospheres and the weight of recovered product was 82.5 grams. Analysis of the product gave 14.7 grams methanol, 1.0 gram methyl formate, 0.2 g ethanol and 0.6 gram ethylene glycol.

Example 113

Example 86 was repeated except that instead of magnesium acetate, cesium carbonate (15.0 m moles) was used and the reaction temperature was 215°C. Total gas uptake was 487 atmospheres and the recovered product weight was 87.8 grams. Analysis of the product gave 16.2 grams methanol, 1.0 gram methyl formate, 0.2 gram ethanol and 0.6 gram ethylene glycol.

Example 114

Example 86 was repeated except that instead of magnesium acetate, cesium hydroxide was used and the reaction temperature was 215°C. Total gas uptake was 33 atmospheres and the recovered product weight was 74.3 grams. Analysis of the product gave 7.5 grams methanol, 0.4 gram methyl formate, 0.1 gram ethanol and 0.3 gram ethylene glycol.

Example 115

Example 86 was repeated except that instead of magnesium acetate, benzyltrimethylammonium acetate (20.0 m moles) was used. Total gas uptake was 333 atmospheres and the recovered product weight was 72.2 grams. Analysis of the product showed 7.6 grams methanol, 0.5 gram methyl formate, 0.2 gram ethanol, 1.0 gram ethylene glycol and 0.2 gram glycerine.

What is claimed is:

1. The process of making an alkane polyol(s) which comprises reacting a mixture consisting essentially of oxides of carbon and hydrogen in the presence of a rhodium carbonyl complex provided to the reaction as a rhodium carbonyl cluster which possesses an infrared spectrum which exhibits three intense wavelength bands between about plus and minus 10 cm$^{116\ 1}$ of about 1868 cm$^{116\ 1}$, about 1838 cm$^{-1}$, and about 1785 cm$^{-1}$ at a pressure between at least about 500 to about 50,000 pounds per square inch absolute and at a temperature of between about 100°C. and about 375°C. sufficient to form such alkane polyol.

2. The process of claim 1 wherein said process encompasses the equilibrium:

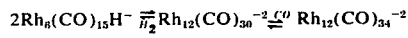

3. The process of claim 1 wherein the rhodium carbonyl cluster is dissolved in an inert diluent.

4. The process of claim 1 wherein the temperature of the reaction is between about 150°C. to about 300°C.

5. The process of claim 4 wherein the temperature of the reaction is between about 190°C. to about 275°C.

6. The process of claim 1 wherein the oxide of carbon is CO and the mol ratio of CO to hydrogen is from about 20:1 to about 1:20.

7. The process of claim 6 wherein the reaction is effected continuously in a tubular reactor.

8. The process of claim 1 wherein the principal products recovered from the reaction are ethylene glycol and methanol.

9. The process of claim 1 wherein the rhodium carbonyl cluster is associated with a counter-ion.

10. The process of claim 9 wherein the counter-ion is an organic ligand compound which organic ligand compound coordinates with said rhodium and contains at least one atom which possesses a pair of electrons which form a coordinate body with rhodium, which atom is at least one of Lewis base nitrogen, Lewis base oxygen and mixtures thereof and the remainder of said compound is carbon and hydrogen.

11. The process of claim 9 wherein the counter-ion is a metal cation.

12. The process of claim 9 wherein the counter-ion is a non-metal cation.

13. The process of claim 1 wherein the rhodium carbonyl cluster is determined by infrared spectrum analysis by passage of the composition to be reacted or the composition at reaction conditions to a heated high pressure infrared cell where such analysis is taken.

14. The process of claim 1 wherein the alkane polyol is a mixture of ethylene glycol, glycerine and 1,2-propylene glycol.

15. The process of claim 1 wherein the alkane polyol is ethylene glycol.

16. The process of claim 3 wherein the diluent is a dialkyl ether of alkylene glycols or polyalkylene glycols.

17. The process of claim 16 wherein the diluent is the dimethyl ether of tetraethylene glycol.

* * * * *

UNITED STATES PATENT OFFICE
CERTIFICATE OF CORRECTION

Patent No. 3,957,857          Dated May 18, 1976

Inventor(s) Roy L. Pruett, and Wellington E. Walker

It is certified that error appears in the above-identified patent and that said Letters Patent are hereby corrected as shown below:

In the claims:

Column 29, line 31, after "minus 10", should read ---$cm^{-1}$--- instead of "$cm^{116}$ 1".

Column 29, line 32, after "about 1868", should read ---$cm^{-1}$--- instead of "$cm^{116}$ 1".

Signed and Sealed this

Twentieth Day of November 1979

[SEAL]

Attest:

RUTH C. MASON
Attesting Officer

LUTRELLE F. PARKER
Acting Commissioner of Patents and Trademarks